United States Patent
Adler

(10) Patent No.: US 7,184,137 B1
(45) Date of Patent: Feb. 27, 2007

(54) AERIAL RETICLE INSPECTION WITH PARTICLE BEAM CONVERSION

(75) Inventor: David L. Adler, San Jose, CA (US)

(73) Assignee: KLA-Tencor Technologies Corporation, Milpitas, CA (US)

( * ) Notice: Subject to any disclaimer, the term of this patent is extended or adjusted under 35 U.S.C. 154(b) by 415 days.

(21) Appl. No.: 10/702,524

(22) Filed: Nov. 6, 2003

Related U.S. Application Data

(60) Provisional application No. 60/499,156, filed on Aug. 29, 2003.

(51) Int. Cl.
G01N 21/00 (2006.01)
H01L 27/00 (2006.01)

(52) U.S. Cl. .............................. 356/237.2; 356/237.5; 250/208.1; 250/311

(58) Field of Classification Search ........ 356/121–127, 356/237.1–237.5; 250/208.1, 311
See application file for complete search history.

(56) References Cited

U.S. PATENT DOCUMENTS

| 4,247,203 | A | | 1/1981 | Levy et al. |
| 5,737,072 | A | | 4/1998 | Emery et al. |
| 6,002,740 | A | * | 12/1999 | Cerrina et al. ................. 378/43 |
| 6,054,713 | A | * | 4/2000 | Miyake et al. ......... 250/492.24 |
| 6,335,783 | B1 | | 1/2002 | Kruit |
| 6,906,305 | B2 | * | 6/2005 | Pease et al. ............. 250/208.1 |
| 7,032,208 | B2 | * | 4/2006 | Yamashita .................... 716/19 |
| 2004/0159787 | A1 | * | 8/2004 | Nakasuji et al. ............ 250/311 |

* cited by examiner

Primary Examiner—Hoa Q. Pham
(74) Attorney, Agent, or Firm—Okamoto & Benedicto LLP

(57) ABSTRACT

One embodiment disclosed relates to an apparatus for inspecting or revieiwing a mask or reticle. The apparatus includes at least an optical system, a converter plate, and an electron system. The optical system projects an optical illumination onto the mask. The optical signal from the mask is received by the converter plate. The converter plate transforms the optical signal to a corresponding electron signal. The electron signal is imaged by the electron system.

13 Claims, 4 Drawing Sheets

(Background)

AERIAL RETICLE INSPECTION WITH PARTICLE BEAM CONVERSION

CROSS-REFERENCE TO RELATED APPLICATIONS

The present application claims the benefit of provisional patent application No. 60/499,156, filed Aug. 29, 2003, entitled "Aerial Reticle Inspection with Particle Beam Conversion", by inventor David L. Adler, the disclosure of which is hereby incorporated by reference.

BACKGROUND OF THE INVENTION

1. Field of the Invention

The present invention relates to apparatus and methods for inspection or review. More particularly, the invention relates to apparatus and methods for inspection or review of reticles or masks used to manufacture semiconductor devices.

2. Description of the Background Art

One of the major sources of yield loss in the manufacture of very large scale integrated (VLSI) circuits is random defect in the photomasks. As chip sizes and geometry densities increase more attention must be given to mask quality in order to reduce defects to a level commensurate with acceptable yields.

SUMMARY

One embodiment of the invention pertains to an apparatus for inspecting or reveiwing a mask or reticle. The apparatus includes at least an optical system, a converter plate, and an electron system. The optical system projects an optical illumination onto the mask. The optical signal from the mask is received by the converter plate. The converter plate transforms the optical signal to a corresponding electron signal. The electron signal is imaged by the electron system.

DETAILED DESCRIPTION

Figure 1:
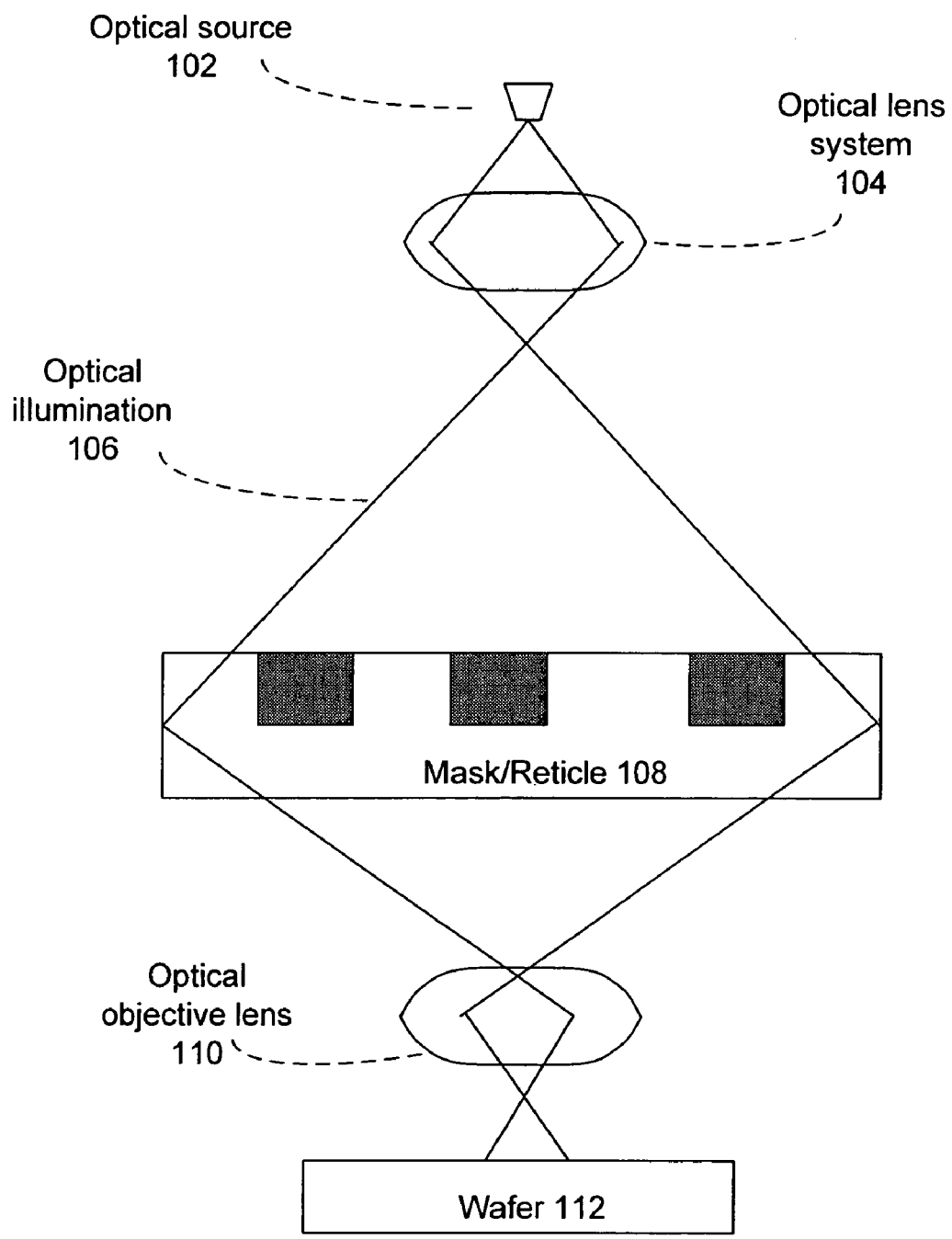
FIG. 1 is a schematic diagram depicting a conventional apparatus for illuminating a wafer with a pattern from a mask or reticle.

FIG. 1 is a schematic diagram depicting a conventional lithography apparatus for illuminating a wafer with a pattern from a mask or reticle. An optical source 102 generates light for illuminating the mask 108. An optical lens system 104 directs and focuses the optical illumination 106 onto the mask 108.

The mask 108 may comprise, for example, a phase shift type mask. The mask 108 transforms the illumination depending upon the patterning thereon. Typically, the patterning on the mask 108 is designed to form a particular pattern on a photoresist layer on the wafer 112.

The illumination passing through and transformed by the mask 108 is focused by an objective lens 110 onto the surface of the wafer 112. The image projected on the wafer may be a fraction in scale (for example, one fourth in scale) compared with the scale of the pattern on the mask 108.

Figure 2:
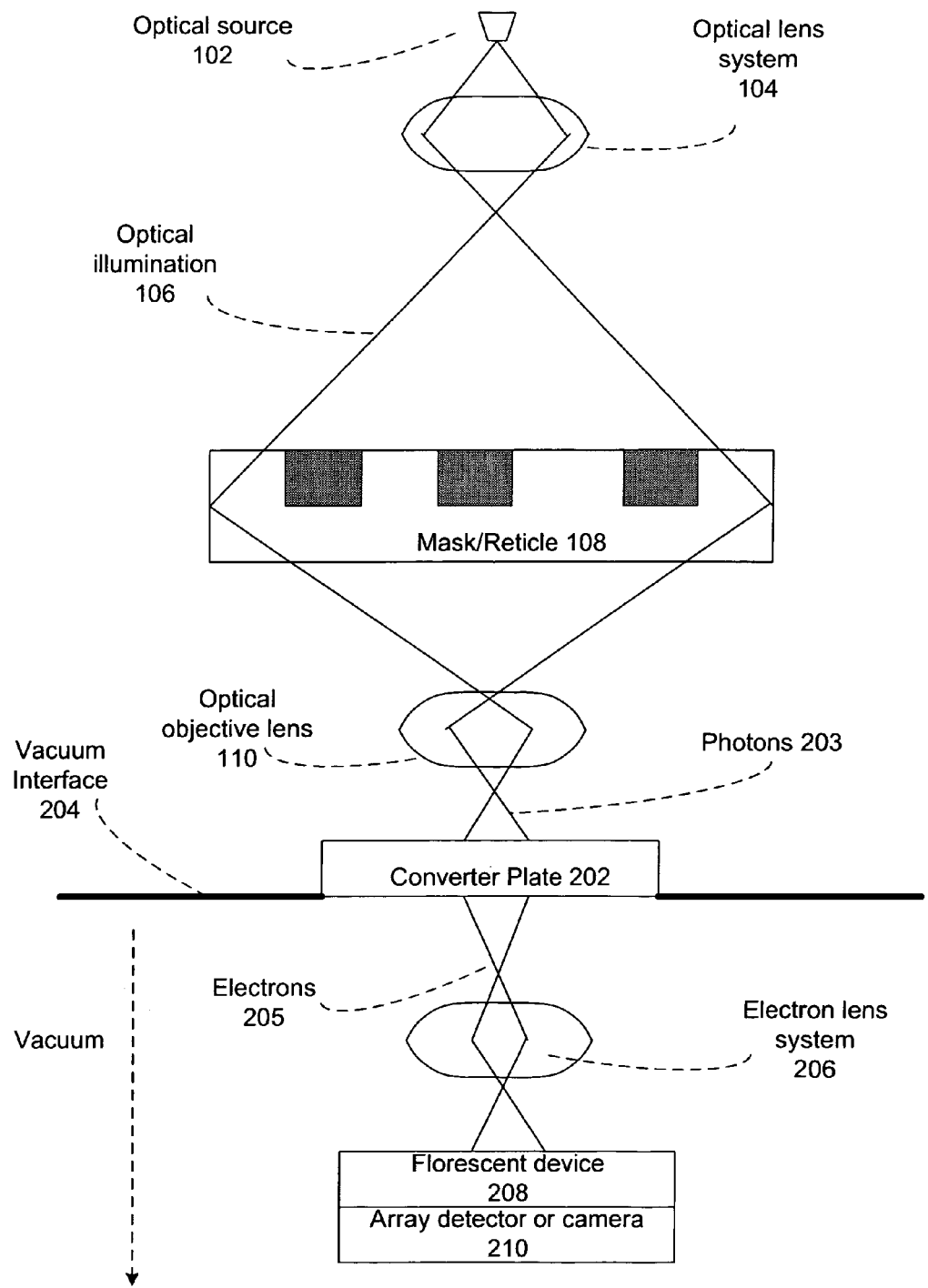
FIG. 2 is a schematic diagram depicting an apparatus for inspecting or reviewing a mask or reticle in accordance with an embodiment of the invention.

FIG. 2 is a schematic diagram depicting an apparatus for inspecting or reviewing a mask or reticle in accordance with an embodiment of the invention. The inspection apparatus depicted in FIG. 2 enables the inspection of the mask 108 to be performed at a one times (1x) magnification in comparison to the eventual patterning on a wafer. In other words, the inspection or review may be performed using the same optical illumination and focusing system as that used in the lithography apparatus. This advantageously eliminates the need to perform complex phase shift related calculations and the errors and inaccuracies that may arise therefrom. Further, the use of a particle beam subsystem in accordance with an embodiment of the invention enables higher resolution inspection than may be obtained by optical means.

The upper optical portion of the inspection apparatus in FIG. 2 may have the same configuration as the corresponding portion of the lithography apparatus in FIG. 1. An optical (or x-ray) source 102 generates light for illuminating the mask 108. An optical lens system 104 directs and focuses the optical illumination 106 onto the mask 108. The illumination passing through and transformed by the mask 108 is focused by an objective lens 110. However, instead of being focused onto the surface of a wafer 112, the illumination is focused onto a converter plate 202.

The converter plate 202 comprises a device that converts the optical-based signal into an electron-based signal. For example, the converter plate 202 may be constructed using commercially available photoelectron material. Night vision goggles may also be constructed using such photoelectron material. Such photoelectron material receives photons 203 and emits electrons 205 in response thereto.

The electron signal 205 is directed and focused by an electron lens system 206 onto a fluorescent device 208. The fluorescent device 208 may include a phosphor based material which receives the electrons and emits light in response thereto. In other words, while the converter plate 202 converts a light signal to an electron signal, the fluorescent device 208 converts an electron signal back to a light signal. Coupled to the fluorescent device 208 is an optical detector or camera 210. The detector 210 may comprise, for example, an array of detector elements, such as a charge-coupled device (CCD) array. In one embodiment, the detector 210 may comprise a time-delay integration (TDI) detector. Such a TDI detector may be used to efficiently inspect a mask 108 while the mask 108 is in linear motion.

In an alternate embodiment, instead of using both a fluorescent device 208 and an array detector 210, a back-thinned array detector may replace both devices. Such a back-thinned array detector may be configured to directly detect electrons, such that the fluorescent conversion of electrons to light is no longer needed. Advantageously, this would eliminate the need for the fluorescent device 208. Disadvantageously, such a back-thinned array detector may be more prone to damage from the electrons and so may not be as robust.

In one embodiment, the detected image data may be compared to images taken from other mask regions to detect defects or process variations. In another embodiment, the detected image data may be compared to a rendered database to detect defects or process variations.

Figure 3:
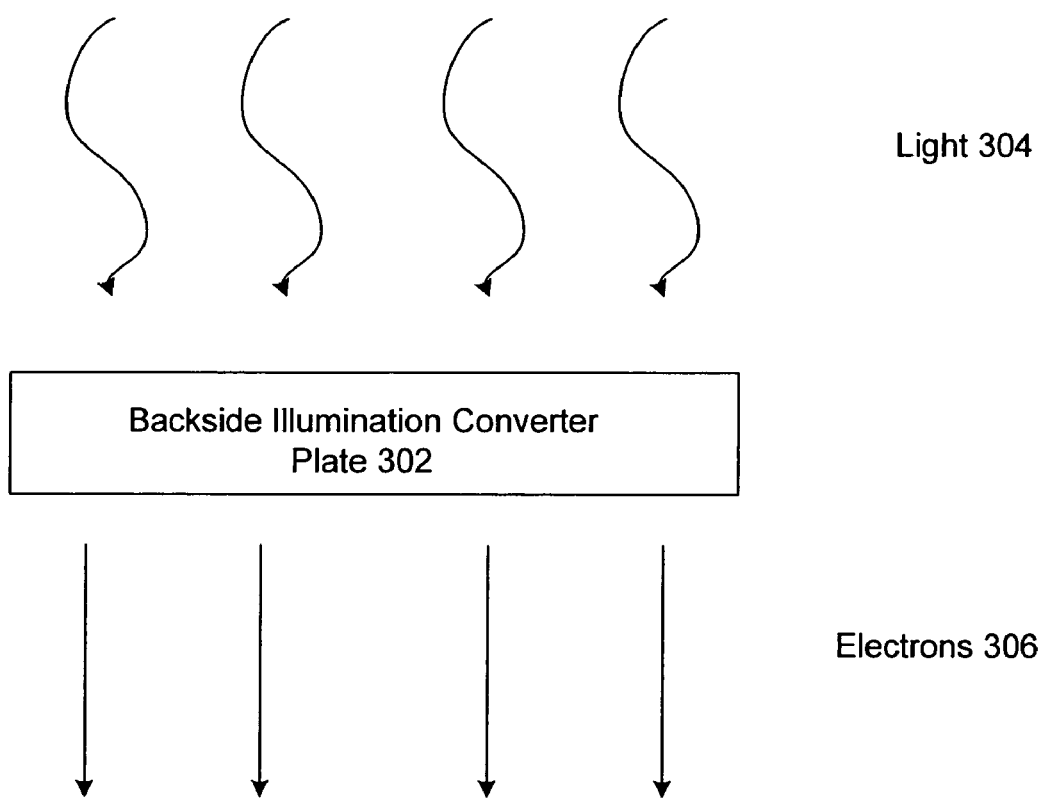
FIG. 3 illustrates such a backside illumination converter plate.

In the configuration depicted in FIG. 2, the converter plate 202 comprises a backside illumination type device. FIG. 3 illustrates such a backside illumination converter plate. As shown in FIG. 3, the backside illumination converter plate 302 receives an optical signal 304 on one side of the plate 302 and emits a corresponding electron signal 306 on the opposite side of the plate 302. Advantageously, the backside illumination converter plate 302 may comprise part of a vacuum interface 204. The vacuum interface 204 separates the optical portion of the system which does not need to be in vacuum from the electron portion of the system which needs to be in vacuum.

Figure 4:
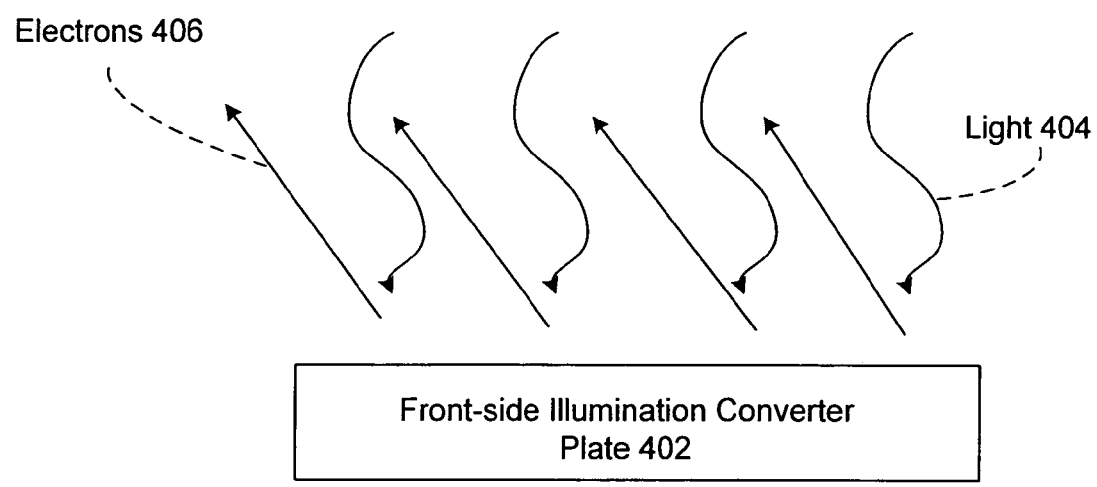
FIG. 4 illustrates such a front-side illumination converter plate.

In contrast, a front-side illumination converter plate 402 is depicted in FIG. 4. As shown in FIG. 4, the front-side illumination converter plate 402 receives an optical signal 404 on one side of the plate 402 and emits a corresponding electron signal 406 on the same side of the plate 402.

An alternate embodiment of the invention may utilize a front-side illumination converter plate 402. In such an embodiment, the electron lens system 206 and the electron imaging devices would be configured on the same side of the converter plate 202 as the optical illumination and focusing components. A field (such as a magnetic field) may be utilized to bend the emitted electrons towards the electron lens system 206. In addition, the apparatus would be configured such that the emitted electrons traveled through a volume pumped by a vacuum.

The above-described diagrams are not necessarily to scale and are intended be illustrative and not limiting to a particular implementation. The above-described invention may be used in an automatic inspection or review system and applied to the inspection or review of optical or X-ray masks and similar substrates in a production environment.

In the above description, numerous specific details are given to provide a thorough understanding of embodiments of the invention. However, the above description of illustrated embodiments of the invention is not intended to be exhaustive or to limit the invention to the precise forms disclosed. One skilled in the relevant art will recognize that the invention can be practiced without one or more of the specific details, or with other methods, components, etc. In other instances, well-known structures or operations are not shown or described in detail to avoid obscuring aspects of the invention. While specific embodiments of, and examples for, the invention are described herein for illustrative purposes, various equivalent modifications are possible within the scope of the invention, as those skilled in the relevant art will recognize.

These modifications can be made to the invention in light of the above detailed description. The terms used in the following claims should not be construed to limit the invention to the specific embodiments disclosed in the specification and the claims. Rather, the scope of the invention is to be determined by the following claims, which are to be construed in accordance with established doctrines of claim interpretation.

What is claimed is:

1. An apparatus for inspecting a mask, the apparatus comprising:
   an optical system for projecting an optical illumination across a width of the mask while the mask is in linear motion;
   a converter plate for receiving a focused optical image from the illuminated width and transforming the optical image to a corresponding electron image;
   an electron lens system for focusing the electron image; and
   a time-delay integration detector system for receiving the electron image while the mask is in linear motions,
   wherein the apparatus is configured for inspecting the mask at a one times (1×) magnification in comparison to eventual patterning on a wafer.

2. The apparatus of claim 1, wherein the converter plate comprises a backside illumination converter plate.

3. The apparatus of claim 2, wherein the backside illumination converter plate comprises at least part of a vacuum interface.

4. The apparatus of claim 1, wherein the converter plate comprises a front-side illumination converter plate, and further comprising a bending device to bend a trajectory of electrons emitted from the converter plate.

5. The apparatus of claim 1, further comprising a vacuum interface between the optical system and the electron lens system.

6. The apparatus of claim 1, wherein the detector system includes a fluorescent device coupled to an array detector.

7. The apparatus of claim 1, wherein the detector system includes an array detector that is adapted to directly detect electrons.

8. A method of inspecting a reticle, the method comprising:
   projecting an optical illumination onto the reticle to produce an optical signal from the reticle while the reticle is in linear motion;
   receiving the optical signal and converting the optical signal to a corresponding electron signal; and
   imaging the electron signal by a time-delay integration detector system,
   wherein the reticle is inspected at a one times (1×) magnification in comparison to eventual patterning on a wafer.

9. The method of claim 8, wherein the optical signal is received on one side of a converter plate, and the corresponding electron signal is emitted on an opposite side of the converter plate.

10. The method of claim 8, wherein the optical signal is received on one side of a converter plate, the corresponding electron signal is emitted on a same side of the converter plate, and the electron signal is bent using a bending device.

11. The method of claim 8, wherein the electron signal is emitted in a vacuum.

12. The method of claim 8, wherein the electron signal is imaged using a fluorescent device to convert the electron signal back to an optical form, and the optical form is detected by an array detector coupled to the fluorescent device.

13. The method of claim 8, wherein the electron signal is imaged using an array detector that is adapted to directly detect electrons.

* * * * *